United States Patent [19]

De Santis

[11] 4,211,392
[45] Jul. 8, 1980

[54] ADJUSTABLE HOLDER FOR MOLDING DENTURES

[76] Inventor: Richard De Santis, 3533-12th Ave., Brooklyn, N.Y. 11218

[21] Appl. No.: 5,166

[22] Filed: Jan. 22, 1979

[51] Int. Cl.² ............................................ B25B 1/20
[52] U.S. Cl. ..................................... 269/75; 269/119
[58] Field of Search .................... 269/71, 75, 111, 113, 269/114, 118, 119, 45, 246, 101; 32/1; 249/219 R, 120, 137, 139, 54

[56] References Cited

U.S. PATENT DOCUMENTS

| | | | |
|---|---|---|---|
| 91,309 | 6/1869 | Dean | 269/75 |
| 260,396 | 7/1882 | Hunt . | |
| 288,300 | 11/1883 | Borowsky | 269/119 |
| 783,031 | 2/1905 | Fell . | |
| 1,036,441 | 8/1912 | Buck | 269/71 |
| 1,446,811 | 2/1923 | Rowland | 269/75 |
| 1,875,761 | 9/1932 | Power . | |
| 2,095,665 | 10/1937 | Greth | 269/75 |
| 2,221,108 | 11/1940 | Rathbun | 269/71 X |
| 2,324,803 | 7/1943 | Snyder | 269/75 X |
| 2,669,958 | 2/1954 | Sweeney | 269/71 X |
| 3,148,873 | 9/1964 | Chandler | 269/71 |

FOREIGN PATENT DOCUMENTS 863736   7/1949   Fed. Rep. of Germany ........... 269/114

*Primary Examiner*—Robert C. Watson

[57] ABSTRACT

In a preferred embodiment, extending upwardly from an anchoring base, a first upright rod is revolvably mounted in the base and at an upper end of the first upright rod there is swivelly mounted a lower end of a second rod having at its distal end a swivelly mounted holder structure which includes box-like vessel four walls each having mounted therethrough male-threaded screw-like clamps having swivelly-mounted gripping structures on the interior ends of the clamps extending inwardly toward one-another into space within which an object to be held and supported will be gripped by the opposing clamps and gripping structures thereof, the swivelly-mounted rod and holder being each alternately securable to a locked position and state, and released to a movable adjustable state, and the first upright rod being also alternately securable to a locked non-revolvable position and state, and releasable to a freely revolvable and thereby adjustable state, such that the object to be held and supported may be positioned as desired during working steps.

2 Claims, 6 Drawing Figures

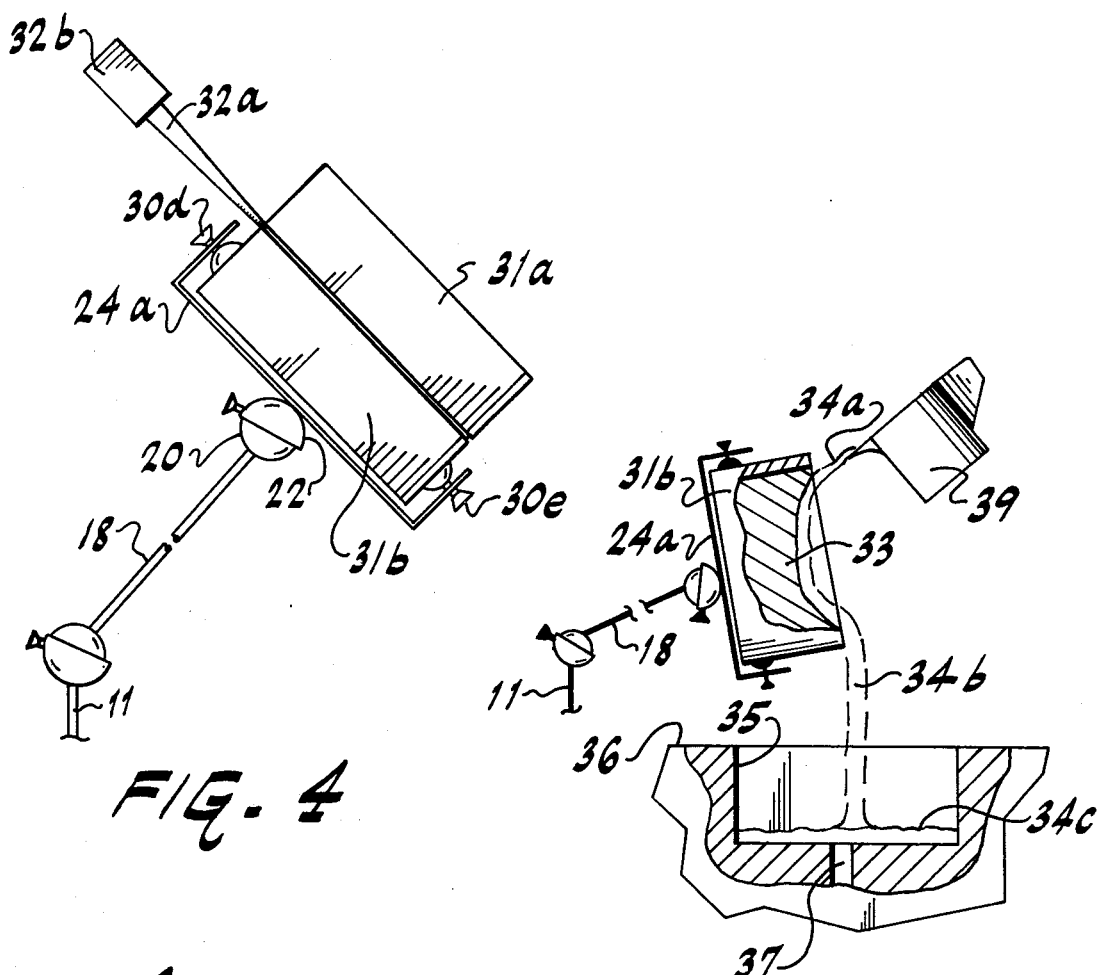
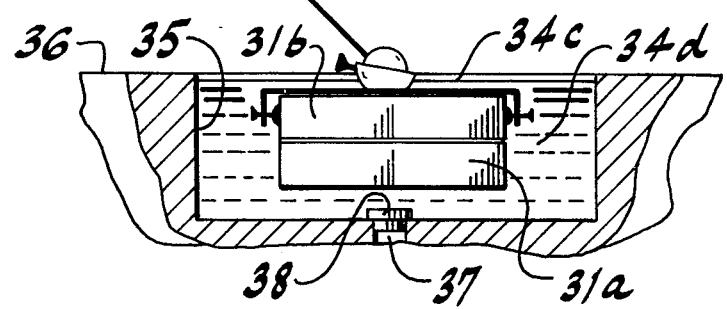
FIG. 4
FIG. 5
FIG. 6

ADJUSTABLE HOLDER FOR MOLDING DENTURES

This invention is directed to a novel holder of a dental mold flask holder together with having multiple other associated uses.

BACKGROUND TO THE INVENTION

Prior to the present invention, there has not existed in the technology of denture molding any suitable holder which would simplify the technique or render easier the task of steps involved in producing dentures. The adjustable holder of the present invention was devised by the present inventor as a part of his work professionally involved in this field of technology, to meet the long felt need experienced by himself and others. While a patentability search turned-up some variety of holders, even one of superficial similarity (Fell U.S.Pat. No. 783,031—directed to a pipe-supporting device), such devices were not of a nature that could be substituted for the present invention, and would not be for comparable utilities nor in the same or related technologies, apart from both being directed to a holding function. Accordingly, the invention as defined in the present patent application are distinctive of additional necessary element which characterize the technology of dental molding, insofar as the present adjustable holder and its use in that technology.

SUMMARY OF THE INVENTION

Accordingly, objects of the present invention include the overcoming of needs and difficulties of the nature discussed-above.

Another and more particular object is to obtain an adjustable holder having a holder structure and mechanism thereof adapted to hold a dental mold flask at various stages of the denture-producing procedure.

Another object is to include in combination with a particularly-designed clamping structure of the holder, a special arrangement of swivel rods.

Another object is to further add a revolving feature with a locking capability, in combination with swivel features of supporting rods for the holder.

Another object is to provide an adjustable holder adaptable to washing-out a mold conveniently.

Another object is to provide an adjustable holder adaptable to facilitating a denture held within a mold in an opened flask.

Another object is to provide an adjustable holder adaptable to positioning and holding a dental mold flask during a wedge-parting of the bottom and top of the flask.

Another object is to provide an adjustable holder adaptable to easily and conveniently immersing a dental mold flask into and within boiling water within a vessel such as a sink or the like.

Other objects become apparent from the preceding and following disclosure.

One or more objects of the invention are obtained by the invention as typically illustrated in the accompanying drawings which are not intended to represent all possibilities nor to unduly limit the scope of the invention, but are intended to enhance understanding of the nature and heart of the invention as set forth in this Specification and claimed in the appended claims.

Broadly the invention may be described as a combination of an anchoring base, an upright rod mounted on the anchoring base, a second rod swivelly mounted at its lower end onto an upper end of the upright rod, and a holder with gripping clamps, swivelly mounted onto a distal end of the second rod, together with locking mechanisms for alternately locking and unlocking each of the swiveling second rod and the holder, for alternate fixed-position and adjusting states; the clamping mechanism is by way of an important arrangement for proper stability and sturdiness against shifting and necessary because of the heavy nature of the objects to be grasped and supported in the practice of the intended use in the holding of dental mold flasks, and accordingly includes substantially parallel supports from which at least one thereof an adjustable clamp is movable and is mounted thereon, in order to grip toward the other opposing support having a gripping face.

Preferably each of at least two opposing supports, i.e. a single set of supports, has an adjustable clamp mounted therethrough such that they are clampable toward each other grippingly.

In a still further preferred embodiment, for more secure grasping and sturdiness, there are provided atleast two sets of these parallel supports, the second set being longitudinally alligned in a direction transverse substantially to the first set, preferably in the nature of a four-sided circumscribing box having a bottom thereof swivelly mounted onto the distal end of the above-noted second rod. In each set, the adjustable clamps of opposing supports are movable grippingly toward one-another so as to grip an object therebetween within the circumscribed space circumscribed by the joined walls of the two sets.

In a preferred type of clamps noted-above, each clamp includes an axially screwable threaded shaft having a gripping structure swivelly mounted on the inwardly extending distal end thereof such that the gripping structure may adjust to any of varying angles of the surfaces of the object to be gripped between opposing gripping structures, with the screwable threaded shaft preferably being male threaded and screwed through a female-threaded aperture in its respective support structure.

In a still further preferred embodiment, the upright rod mounted on the anchoring base, is revolvably mounted and there is included a locking mechanism such that when unlocked it may be revolved freely to a preferred position, but when locked is non-revolvable thus fixing non-movably the position of the upright rod and of other locked structure thereof above-described.

The support base, or anchoring base, may be a very heavy base sufficiently heavy as to prevent tilting when heavy objects are grasped and supported by the holder and clamps and gripping structures thereof. On the other hand, the anchoring base may be mounted by a male threaded shaft element adapted for fastening the base structure to a substrate surface such as a table top or edge; typically, a screw may secure the same to the table top by screwing the same into the table top, or alternately such threaded shaft element may be a part of a table edge or desk edge clamping mechanism clamping onto the table or desk as an anchoring mechanism. The gripping surfaces are preferably recessed.

The invention may be better understood by making reference to the following Figures.

THE FIGURES

FIG. 1 illustrates a side view in-part and perspective view in-part, of a preferred embodiment of the present invention, with partial cut-away for improved illustration.

FIGS. 4 through 6 all merely symbolically illustrate the structure of the adjustable holder of the invention, and are principally for illustrating variying uses and other embodiments of the holder, while FIGS. 2 and 3 are mere in-part view illustrations of alternate anchoring base embodiments.

More particularly, the FIG. 2 illustrates an in-part view in side view of a large and heavy support base sufficiently large and weighted as to avoid tilting of the upright and illustrated rod.

In like manner, the FIG. 3 is an in-part view in side view of a table-edge or desk-edge with the anchoring base clamped thereon.

FIG. 4 illustrates a slightly-tilted holder in a fixed-state in side view—with the front side cut-away or not shown in order to improve clarity of illustration, with the gripping surfaces gripped onto a bottom half of an entire and assembled top and bottom flask, also symbolically illustrating a step of wedging a wedge blade therebetween in order to cause the top to part from the bottom, for the flasks. Its half-shell mounts the holder bottom.

FIG. 5 is a FIG. 4 type of symbollically illustrated holder, showing a severely tilted fixed state of the held lower flask containing the mold, in a state of being washed while held in a fixed position above a sink or other vessel, cut-aways serving to improve understanding of the illustration.

FIG. 6, like FIG. 5, shows in side and cut-away view a utility of supporting both the top and bottom (such as FIG. 4) but in an inverted position and downwardly within boiling water in a sink or other vessel. Its half-shell mounts the holder bottom.

DETAILED DESCRIPTION

In greater detail, all Figures represent the same preferred embodiments of various preferred features noted above, and accordingly for different figures common indicia are utilized in sofaras is possible, for clarity of identification, but with modifications such as 30a, 30b, and the like, permitting separate discussion and identification where desired for purposes of description and discussion.

Figure 1:
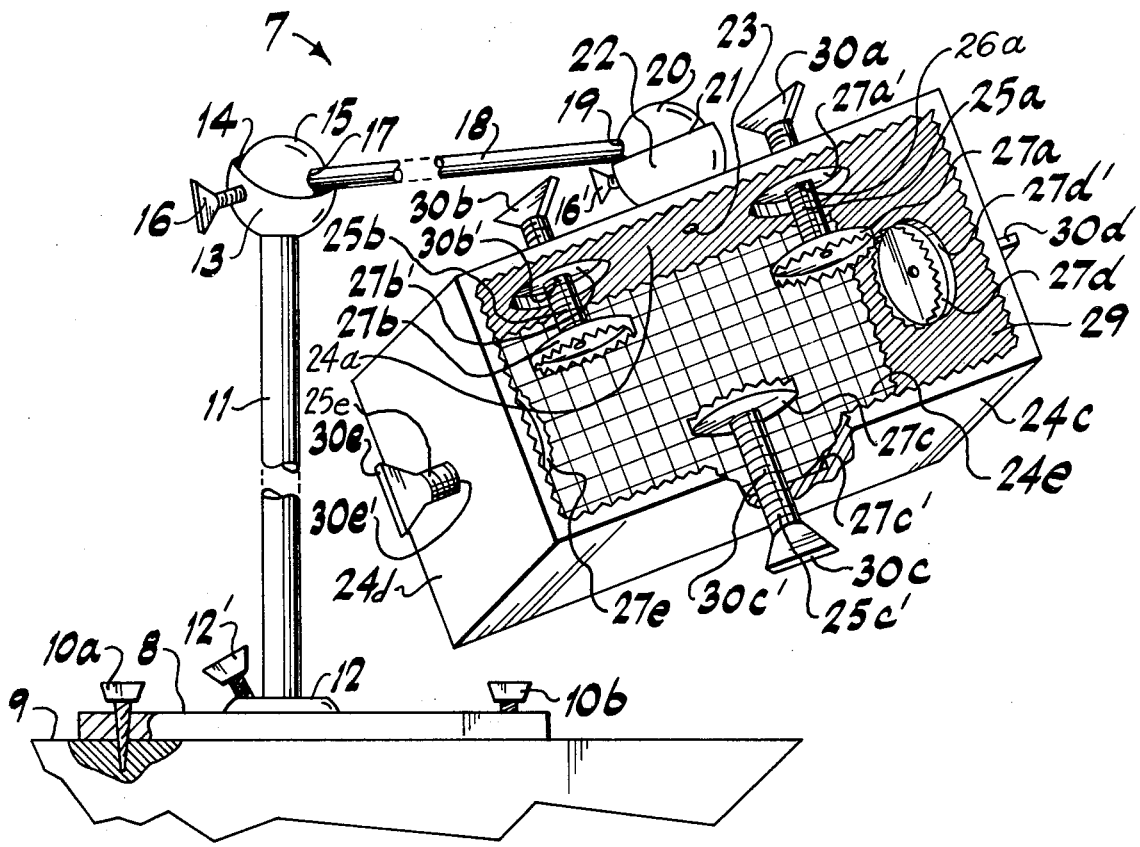

FIG. 1 shows in detail an entire embodiment of the adjustable dental mold flask holder 7 having its anchoring base 8 anchored to a substrate surface 9 such as a table or bench top, by anchor male-threaded screw 10a and screw 10b. The anchoring base 8 has mounted thereon upright rod 11 mounted by mounting structure and mechanism 12 which attaches the rod in a manner allowing the rod 11 to revolve freely in either clockwise or counter-clockwise directions when the set-screw (lock) 12' is in a released state, but which is lockable to a non-revovable rod state by turning the lock screw 12' typically clockwise to lock or set the screw. Thus the mounting structure and mechanism 12 mounts the rod 11 onto the anchoring base 8.

On an upper end of the rod 11, there is swivelly mounted the lower or proximal end of the second rod 18 having the lower end thereof mounted within hole 17 of revolvable and swiveling ball 15 mounted swivelly within the socket 14 of the outer substantially half-shell 13 into which the upper end of the upright rod is mounted within the half-shell hole 12, the freely swiveling ball 15 being lockable to a non-movable position and state by a tightening or turning of the lock screw 16 typically clockwise in direction to lock and counter-clockwise to unlock. Note the preferslant on the upper surface of the half-shell 13 which has the preferred function of permitting the rod 18 to lean downwardly further than otherwise would be possible, this function and advantabe being in conjunction and combination with the function and combination of the revolvable nature of upright rod 11 which freely turns such that the low-point of the edge of the half-shell may be on any side-direction prior to locking the lock-screw 12'.

While the half-shell 13 has been labeled with that name, it is to be recognized that this swivel joint is of any desired and/or conventional type and that the shell may be more or less than "half" a sphere, but is typically more than half as is shown in this embodiment; the raised edge of the half-shell has the advantage of more adequately providing room for and improved functioning of the lock-screw 16.

Likewise, the half-shell 22 and the ball 20 in socket 21, and the second rod's upper end (distal end) mounted in ball hole 19, and the half-shell attached to holder wall 24a by brad 23, fuction and are substantially the same as that of the swivel structure and mechanism above-noted for ball 15 and half-shell 13, and the like, thus requiring no further discussion, except noting that the lock-screw 16' thereof serves to lock and unlock it to and from a locked position and state to and from a freely swiveling state.

The holder typically comprises opposed parallel walls 24a and 24c as one set of parallel supports, and opposed parallel walls 24b and 24d as a second set of parallel supports extending longitudinally in a direction substantially transverse to the longitudinal axes of the parallel support walls 24a and 24c, thereby forming a four-sided box of typically rectangular shape having a screen bottom 24e thereto (but not necessarily having such bottom) even though such is preferred to offer greater support to the held object, as well as serving to reinforce the support walls 24a through 24d adding durability thereto needed in view of the very heavy objects required to be held by the holder of this invention in serving to accomplish its intended utility of use in the dental molding technology above-noted. While the half-shell 22 is shown anchored to the support wall 24a, it is also possible that it may be anchored to some one or more other support wall(s) and/or bottom 24e, as might be desired or necessary to add improved strength and further durability.

In a further preferred embodiment, the inner wall surface of 24a through 24d have corresponding recesses 27a', 27b', 27c', 27d' for recessed seating of the respective gripping surfaces 27a through 27d respectively. Also, as will be noted in the FIG. 1 illustration, the inner face of the wall surfaces 24a through 24d have toothed or otherwise irregular surfaces adapted to readily serve as gripping surfaces, such that when one of the opposing gripping surfaces is fully recessed, the corresponding support thereof may serve as a gripping surface when the opposing gripping movable surface is advanced toward it to push the object thereagainst, if and when desired for improved variety and choice of ways to use to fit and fulfill particular needs of different situations as they may arise.

Accordingly, the respective axially screwable threaded shafts such as 25a, 25b, 25c, and 25e are mounted through female-threaded apertures (holes) 30a', 30b', 30c', and 30e' of the respective walls 24a, 24b, 24c, and 24e, all such shafts and apertures being viewable in FIG. 1. By tightening (typically turning clockwise) these shafts, the gripping surfaces(of grippers) 27a through 27e are moved inwardly toward opposing ones of the parallel supports and gripper(s) gripping surfaces thereof, to grip any object located within the gripping-space 29 adjacent the bottom wall 24e.

As may be seen for the gripping surfaces (and overall gripper structure thereof) 27a and 27b, there is an anchoring brad or key 28, or the like, loosely anchoring it (the gripper structure) to the terminal end of the threaded shaft 25a, for example, permitting wobbling, i.e. permitting the gripping surface to adjust to varying angles of surfaces to be gripped, whether that surface by planar, concave, slanted, convex, or the like.

Figure 2:
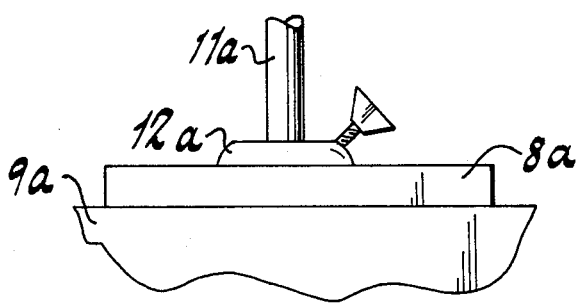

FIG. 2 illustrates a large and heavily-weighted anchoring base structure 8a of sufficient mass to prevent tilting of the upright rod 11a and base structure 8a when heavy objects are held by the holder thereof particularly at distant lateral positions which would be inclined to cause tilting. Revolvable mounting structure 12a is also illustrated.

Figure 3:
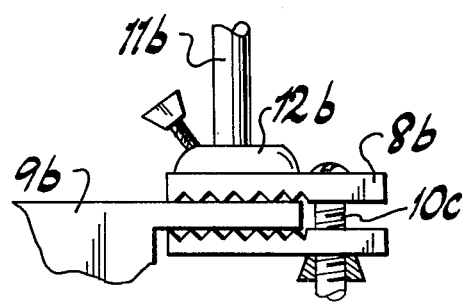

In like manner, FIG. 3 illustrates for substrate surface 9b a table or desk or counter edge having a clamp-anchoring base structure 8b tightened to a gripping and anchoring state by the threaded shaft 10c. The upright rod 11b is revolvably mounted onto the clamp-anchoring base structure 8b by the swivel mounting structure and mechanism 12b.

FIG. 4 shows, in an in-part symbollic view of the adjustable holder 7, the typical fixed-position (i.e. when locked) of the rod 11 and rod 18 and other above-discussed component parts and elements; additionally, however, there is shown in a gripped state a typically appearing gripped assembled top and bottom flasks having therein the mold in a denture molding procedure, with the flasks being held while a wedge blade 32a of handle 32b it utilized to facilitate the parting of the top flask 31a from the bottom flask 31b, the handles such as 30d and 30e having been turned to lock-grip the bottom flask 31b into a securely held position and state. The holder bottom is mounted on a half-shell 22.

FIG. 5 illustrates substantially the same as FIG. 5, except with the holder position at a more severe or greater tilt, illustrating a washing procedure by use of ladel or pitcher 39 pouring water 34a to wash the surface of mold 33, and draining wash-water 34b falling typically into a counter-basin 35 of a counter 36 collecting waste-water 34c draining through drain 37.

FIG. 6 illustrates a further illustration such as that of FIG. 5, illustrating use of the adjustable holder when exposing the upper and lower flasks 31a and 31b to the heat of typically 212 degrees Fahrenheit when immersed within hot water 34d below water surface 34c, with an appropriate plug 38 blocking the drain 37—such basin being merely symbolic of any normally used or preferred vessel or the like in which such immersion would be or might desirably be conducted.

Particular attention is directed to the varying and large variation in angles possible by the present invention, and the beneficial results and utility thereof not heretofore available.

I claim:

1. An adjustable dental mold flask holder device comprising in combination: base means for anchoring securely base structure to a substrate surface; first rod-mounting means for mounting a first rod revolvably onto an upper portion of said base means; a first rod extending longitudinally uprightly having a lower rod end thereof revolvably mounted by said first rod-mounting means onto said base means; first swivel means mounted on an upper rod end of said first rod, for swivelly-mounting a second rod onto said upper rod end, and for alternately securing immovably and releasing for adjusting movement of the second rod; the second rod extending longitudinally away from and having a second rod lower and mounted swivelly on said upper rod end of said first rod by said first swivel means; second swivel means mounted on a second upper rod end of the second rod, and for alternately securing immovably and releasing for adjusting movement of and swivelly mounting a holder structure; and a holder means including the holder structure, for alternately clamping securely onto an object to be held and releasing for removal of or receipt of an object, said holder means including opposing supports extending substantially parallel to one-another and permanently rigidly fixed in spaced-apart relationship to one-another, at least one of said opposing supports having mounted thereon an adjustable clamp movable between alternate clamping positions toward and away from the other one of the opposing supports, the opposing supports and all of said adjustable clamps being jointly positioned and having gripping surfaces such that an object may be securely releasably gripped, said holder means being mounted on said second upper rod end by said second swivel means, said holder means including two of said adjustable clamps in at-least two sets of said opposing supports arranged with the opposing supports of one set extending substantially transversely to another set of the opposing supports and thereby the two sets of opposing supports substantially circumscribing a space within which an object is to be gripped and supported by said adjustable clamps.

2. An adjustable dental mold flask holder device comprising in combination: base means for anchoring securely base structure to a substrate surface, said base means including said base structure and a male threaded shaft element adapted for fastening the base structure to the substrate surface; first rod-mounting means for mounting a first rod revolvably onto an upper portion of said base means; a first rod extending longitudinally uprightly having a lower rod end thereof revolvably mounted by said first rod-mounting means onto said base means; first swivel means mounted on an upper rod end of said first rod, for swivelly-mounting a second rod onto said upper rod end, and for alternately securing immovably and releasing for adjusting movement of the second rod; the second rod extending longitudinally away from and having a second rod lower end mounted swivelly on said upper rod end of said first rod by said first swivel means; second swivel means mounted on a second upper rod end of the second rod, and for alternately securing immovably and releasing for adjusting movement of and swivelling mounting a holder structure; and a holder means including the holder structure, for alternately clamping securely onto an object to be held and releasing for removal of or receipt of an object, said holder means including opposing supports extending substantially parallel to one-another and permanently rigidly fixed in spaced-apart relationship to one-another, at least one of said opposing supports having mounted thereof an adjustable clamp movable between alternate clamping positions toward and away from the other one of the opposing supports, the opposing supports and all of said adjustable clamps being jointly positioned and having gripping surfaces such that an object may be securely releasably gripped, said holder means being mounted on said second upper rod end by said second swivel means, an inner face surface of said opposing supports each having a recess therein within which the adjustable clamp's gripping surfaces are seated when withdrawn, and said inner face surface each having a gripping surface adapted to grip against an object pushed thereagainst.

* * * * *